United States Patent [19]

Angevine et al.

[11] Patent Number: 5,001,295

[45] Date of Patent: * Mar. 19, 1991

[54] PROCESS FOR PREPARING DIALKYLNAPHTHALENE

[75] Inventors: Philip J. Angevine, Woodbury; Thomas F. Degnan, Moorestown; David O. Marler, Deptford, all of N.J.

[73] Assignee: Mobil Oil Corp., Fairfax, Va.

[*] Notice: The portion of the term of this patent subsequent to Feb. 12, 2008 has been disclaimed.

[21] Appl. No.: 494,203

[22] Filed: Mar. 15, 1990

Related U.S. Application Data

[63] Continuation-in-part of Ser. No. 254,524, Oct. 6, 1988, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .............................................. C07C 2/66
[52] U.S. Cl. .................................... 585/467; 585/446
[58] Field of Search ...................... 585/446, 453, 467

[56] References Cited

U.S. PATENT DOCUMENTS

| | | | |
|---|---|---|---|
| 3,775,496 | 11/1973 | Thompson | 260/668 F |
| 4,439,409 | 3/1984 | Puppe et al. | 423/328 |
| 4,774,379 | 9/1988 | Butler et al. | 585/467 |
| 4,795,847 | 1/1989 | Weitkamp et al. | 585/467 |
| 4,826,667 | 5/1989 | Zones et al. | 423/277 |
| 4,899,007 | 2/1990 | Chu et al. | 585/471 |
| 4,899,008 | 2/1990 | LaPierre et al. | 585/467 |
| 4,916,100 | 4/1990 | Knuuttila et al. | 585/467 |

FOREIGN PATENT DOCUMENTS

| | | |
|---|---|---|
| 231860 | 8/1987 | European Pat. Off. |
| 293032 | 11/1988 | European Pat. Off. |
| 3334084 | 4/1985 | Fed. Rep. of Germany |
| 2133032 | 7/1984 | United Kingdom |

*Primary Examiner*—Anthony McFarlane
*Attorney, Agent, or Firm*—Alexander J. McKillop; Charles J. Speciale; Dennis P. Santini

[57] ABSTRACT

A catalytic process is provided for the preparation of dialkylnaphthalenes by alkylating a 2-alkylnaphthalene with an alkylating agent having an aliphatic group of from one to five carbon atoms, such as methanol. The catalyst comprises a synthetic zeolite characterized by an X-ray diffraction pattern including interplanar d-spacings at $12.36 \pm 0.4$, $11.03 \pm 0.2$, $8.83 \pm 0.14$, $6.18 \pm 0.12$, $6.00 \pm 0.10$, $4.06 \pm 0.07$, $3.91 \pm 0.07$ and $3.42 \pm 0.06$ Angstroms.

20 Claims, 2 Drawing Sheets

PROCESS FOR PREPARING DIALKYLNAPHTHALENE

CROSS-REFERENCE TO RELATED APPLICATIONS

This application is a continuation-in-part of U.S. patent application Ser. No. 254,524 filed Oct. 6, 1988, now pending, as a continuation-in-part of U.S. patent application Ser. No. 98,176, filed Sept. 18, 1987, now abandoned, which is a continuation-in-part of U.S. patent application Ser. No. 890,268 filed July 29, 1986, now abandoned. This application is related by subject matter to U.S. patent application Ser. No. 469,998, filed Jan. 25, 1990, and U.S. patent application Ser. No. 494,255, filed concurrently herewith.

BACKGROUND OF THE INVENTION

This invention relates to a process for preparing dialkylnaphthalene, and more particularly to a method for preparing 2,6-dimethylnaphthalene by alkylation of napthalene and/or 2-methylnaphthalene with, for example, methanol using a zeolite catalyst.

The compound 2,6-dimethylnaphthalene (2,6-DMN) is a high valued commodity chemical which, as a precursor to 2,6-naphthalene-dicarboxylic acid, finds use in the manufacture of polyester resins.

Alkylation of naphthalene or 2-methylnaphthalene (2- MN) with methanol or dimethyl either using a zeolite catalyst is known in the art. ZSM-5 is presently a preferred catalyst for this process.

U.S. Pat. No. 4,795,847 (Weitkamp et al.) describes a process for the preparation of 2,6-dialkylnaphthalenes by selectively alkylating naphthalene or 2-alkylnaphthalene with an alkylating agent such as methanol in the presence of a zeolite catalyst. Specifically disclosed is ZSM-5 as the catalyst.

U.S. Pat. No. 3,775,496 (S. L. Thompson) describes a multistep process for converting 5-m-tolyl-pentene-2 to 2,6- dimethylnaphthalene. The 5-m-tolyl-pentene-2 is first converted to a mixture of dimethyltetralins, which are then dehydrogenated to form alkylnaphthalenes. These are then isomerized to form the 2,6-isomer and the 2,7-isomer.

UK Patent GB 2,133,032 describes a method for preparing dimethylnaphthalene by reacting monomethylnaphthalene with methanol over an alumina, silica, or silica-alumina catalyst.

German Patent DE 3,334,084 mentions the alkylation of naphthalene or alkylnaphthalene with methanol.

SUMMARY OF THE INVENTION

Provided herein is a method for producing a 2,6dialkylnaphthalene from a feedstock containing naphthalene or 2alkylnaphthalene and an alkylating agent having an alkylating aliphatic group of from one to five carbon atoms by contacting said feedstock under alkylation conditions with a particular zeolite catalyst composition to produce an alkylate product. The zeolite comprises a synthetic porous crystalline material characterized by an X-ray diffraction pattern including interplanar d-spacings at $12.36 \pm 0.4$, $11.03 \pm 0.2$, $8.83 \pm 0.14$, $6.18 \pm 0.12$, $6.00 \pm 0.10$, $4.06 \pm 0.07$, $3.91 \pm 0.07$ and $3.42 \pm 0.06$ Angstroms.

Alkylation conditions include a temperature of between about 0° C. to 500° C. and preferably between about 240° C. to about 450° C., and a pressure of between 0 to 250 atmospheres and preferably 1 to 25 atmospheres. The molar ratio of alkylating agent to alkylatable aromatic compound (i.e., naphthalene or 2-alkylnaphthalene) can be from about 1:1 to 10:1, and preferably can be from about 3:1 to 5:1. The reaction is suitably accomplished utilizing a feed space velocity of between about 0.1 and 10.0 $hr^{-1}$.

Compared with ZSM-5, the catalyst composition used in the method of the present invention exhibits a higher selectivity for 2,6-dialkylnaphthalene at higher conversions.

DETAILED DESCRIPTION OF THE PREFERRED EMBODIMENTS

Figure 1:
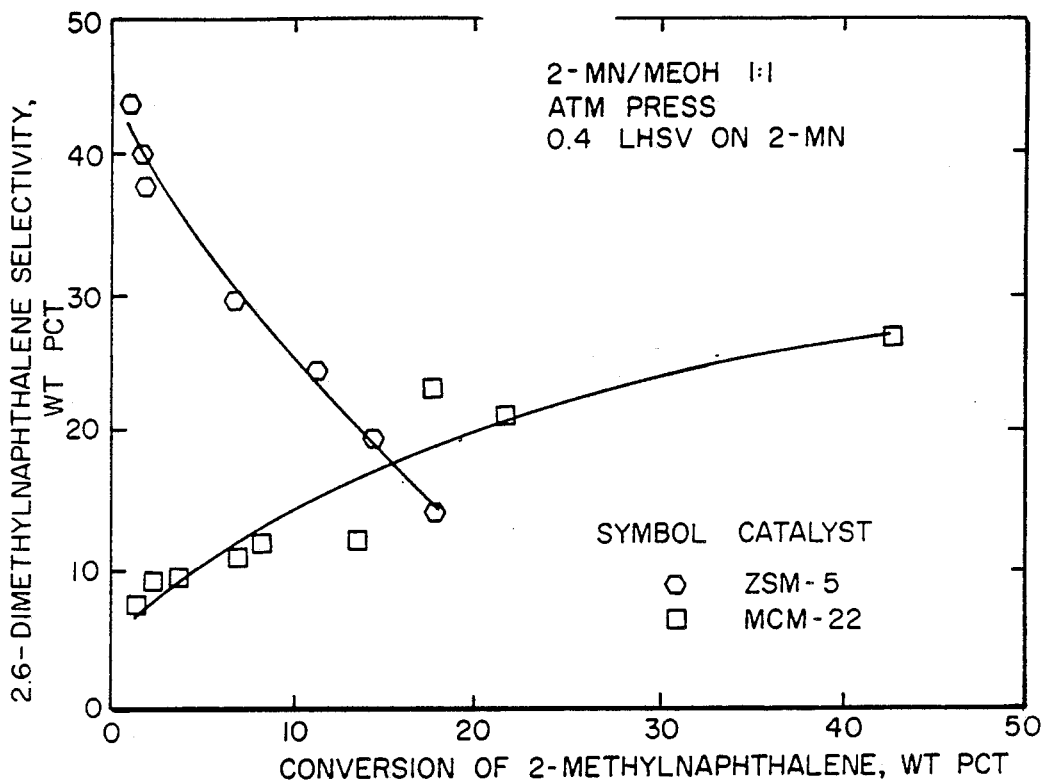
FIG. 1 graphically illustrates the 2,6- dimethylnaphthalene selectivity for the MCM-22 catalyzed embodiment of the present process and a ZSM-5 catalyzed process over a range of conversions.

The entire contents of application Ser. No. 254,524; 98,176, and 890,268 are incorporated herein by reference.

The feedstock used in the process of the present invention is an alkylatable polynuclear aromatic compound, specifically naphthalene or 2-alkylnaphthalene, and preferably 2methylnaphthalene.

Alkylation conditions include a temperature of between about 0° C. to 500° C. and preferably between about 240° C. to about 450° C., and a pressure of between 0 to 250 atmospheres and preferably 1 to 25 atmospheres. The molar ratio of alkylating agent to alkylatable aromatic compound (i.e., naphthalene or 2-alkylnaphthalene) can be from about 1:1 to 10:1, and preferably can be from about 3:1 to 5:1. A preferred molar ratio for methanol/2-methylnaphthalene is 4.5:1. The reaction is suitably accomplished utilizing a feed space velocity of between about 0.1 and 10.0 LHSV, and preferably between about 0.1 to 1.0.

Preferred alkylating agents have an alkylating aliphatic group of from one to five carbon atoms, and can include alcohols (including monoalcohols, dialcohols, and trialcohols), olefins, aldehydes, halides, and ethers. Especially preferred is methanol.

The alkylation can be carried out in any of the known reactors usually employed for alkylation. For example, a tubular reactor with a downflow of reactants over a fixed bed of catalyst can be employed.

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, $I/I_o \times 100$ |
| --- | --- |
| $12.36 \pm 0.4$ | M-VS |
| $11.03 \pm 0.2$ | M-S |
| $8.83 \pm 0.14$ | M-VS |
| $6.18 \pm 0.12$ | M-VS |
| $6.00 \pm 0.10$ | M-M |

TABLE A-continued

| Interplanar d-Spacing (A) | Relative Intensity, $I/I_o \times 100$ |
| --- | --- |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
| --- | --- |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

More specifically, it may be characterized in its calcined form by an X-ray diffraction pattern including the following lines:

TABLE D

| Interplanar d-Spacing (A) | Relative Intensity, $I/I_o \times 100$ |
| --- | --- |
| 30.0 ± 2.2 | W-M |
| 2.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |

TABLE D-continued

| Interplanar d-Spacing (A) | Relative Intensity, $I/I_o \times 100$ |
| --- | --- |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak and d (obs.) the interplanar spacing in Angstrom Units (A), corresponding to the recorded lines, were determined. In Tables A–D, the relative intensities are given in terms of the symbols W=weak, M=medium, S=strong, VS=very strong. In terms of intensities, these may be generally designated as follows:

W = 0–20
M = 20–40
S = 40–60
VS = 60–100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g., silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$X_2O_3:(n)YO_2$, wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$(0.005-0.1)Na_2O:(1-4)R:X_2O_3:nYO_2$ wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400m$^2$/gm as measured by the BET (Bruenauer, Emmett and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Preferred cations are those which tailor the activity of the catalyst. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Prior to its use in the catalyst composition herein, the synthetic porous crystalline material zeolite should be subjected to thermal treatment to remove part or all of any organic constituent present therein.

The zeolite present in the catalyst composition herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the zeolite and/or matrix with which the zeolite may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing the platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 2 hours. While subatmospheric pressure can be employed for the thermal treatment, atmospheric pressure is preferred simply for reasons of convenience. The thermal temperature can be performed at a temperature of up to about 925° C.

Prior to its use in the catalyst composition and process of this invention, the zeolite crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, or organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt.% solid $YO_2$ Where YO is silica, the use of a silica source containing at least about 30 wt.% solid silica, e.g., Ultrasil (a precipitated, spray dried silica containing about 90 wt.% silica) or HiSil (a precipitated hydrated $SiO_2$ containing about 87 wt.% silica, about 6 wt.% free $H_2O$ and about 4.5 wt.% bound $H_2O$ of hydration and having a particle size of about 0.02 micron) favors MCM-22 crystal formation from the above mixture and is a distinct difference over the synthesis method disclosed in U.S. Pat. No. 4,439,409. If another source of oxide of silicon, e.g., Q-Brand (a sodium silicate comprised of about 28.8 wt.% of $SiO_2$, 8.9 wt.% $Na_2O$ and 62.3 wt.% $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt.% solid $YO_2$, e.g., silica, and more preferably at least about 40 wt.% solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 material will vary with the nature of the reaction mixture employed and the crystallization conditions. In all cases, synthesis of the MCM-22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desirable to incorporate the zeolite crystalline material with another material, i.e., a binder, which is resistant to the temperatures and other conditions employed in the process of this invention. Suitable binder materials include active and inactive materials and synthetic or naturally occurring zeolite as well as inorganic materials such as clays, silica and/or metal oxides such as alumina. The latter can be either naturally occurring or provided in the form of gelatinous precipitates or gels including mixtures of silica and metal oxides. Use of a binder material in conjunction with the zeolite, i.e., combined therewith or present during its synthesis, which itself is catalytically active may change the conversion and/or selectivity of the catalyst Inactive materials suitably serve as diluents to control the amount of conversion so that products can be obtained economically and in a controlled fashion without having to employ other means for controlling the rate of reaction.

These materials can be incorporated into naturally occurring clays, e.g., bentonite and kaolin, to improve the crush strength of the zeolite under commercial operating conditions. Good crush strength is an advantageous attribute for commercial use since it prevents or delays breaking down of the catalyst into powder-like materials.

Naturally occurring clays which can be composited with the zeolite crystals include the montmorillonite and kaolin family, which families include the subbentonites, and the kaolines commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

Apart from or in addition to the foregoing binder materials, the zeolite crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may also be advantageous to provide at least a part of the foregoing matrix materials in colloidal form so as to facilitate extrusion of the bound catalyst component(s).

The relative proportions of finely divided crystalline material and inorganic oxide matrix can vary widely with the zeolite content ranging from about 1 to about 95 percent by weight and more usually, particularly when the composite is prepared in the form of beads, in the range of about 2 to about 80 weight percent of the composite.

The stability of the zeolite catalyst may be increased by steaming, with suitable steam stabilization conditions including contacting the catalyst with, for example, 5–100% steam at a temperature of at least 300° C (e.g. 300–650° C.) for at least one hour (e.g. 1–200 hours) at a pressure of 100–2,500 kPa. In a more particular embodiment, the catalyst can be made to undergo steaming with 75–100% steam at 315–500° C. and atmospheric pressure for 2–25 hours.

In order to more fully illustrate the process of this invention and the manner of practicing same, the following examples are presented. In examples which are illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample g/100 g of calcined adsorbant. Zeolite MCM-22 always exhibits Equilibrium Adsorption values of greater than about 10 wt.% for water vapor, greater than about 4.5 wt.%, usually greater than about 7 wt.% for cyclohexane vapor and greater than about 10 wt.% for n-hexane vapor. These vapor sorption capacities are a notable distinguishing feature of zeolite MCM-22 and are preferred for the process of this invention.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant = 0.016 sec$^{-1}$). The Alpha Test is described in U.S. Pat. No. 3,354,078; in the *Journal of Catalysis*, vol. 4, p. 527 (1965); vol. 6, p. 278 (1966); and vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395.

Examples 15, 16, 17, and 18 were carried out in a downflow fixed bed tubular reactor under atmospheric pressure at temperatures ranging from 247° C. to 450° C. Methanol and 2-methylnaphthalene were fed to the reactor by two separate high pressure liquid chromatographic (HPLC) pumps at a 1:1 wt ratio (4.5:1 molar ratio) of methanol to 2-methylnaphthalene. Liquid hourly space velocities were 0.49/hr for methanol and 0.4/hr for 2-methylnaphthalene.

The reaction products were collected in a series of traps comprised of a heated (100° C.) vessel, a room temperature trap, and a gas sampling vessel. Typical mass closures were better than 98.5%. Products were measured by capillary gas chromatography. The various isomers of dimethylnaphthalene were identified by GC-mass spectrometry and confirmed by doping a commercially available mixture of dimethylnaphthalenes with pure isomers.

EXAMPLE 1

One part sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (90% $SiO_2$). The reaction mixture had the following composition, in mole ratios:

$SiO_2/Al_2O_3 = 30.0$
$OH^-/SiO_2 = 0.18$
$H_2O/SiO_2 = 44.9$
$Na/SiO_2 0.18$
$R/SiO_2 = 0.35$ where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

$H_2O$ : 15.2 wt.%
Cyclohexane : 14.6 wt.%
n-Hexane :16.7 wt.%

The surface area of the zeolite was measured to be 494 $m^2/g$.

The chemical composition of the uncalcined material was determined to be as follows:

| Component | wt. % |
| --- | --- |
| $SiO_2$ | 66.9 |
| $Al_2O_3$ | 5.40 |
| Na | 0.03 |
| N | 2.27 |
| Ash | 76.3 |
| $SiO_2O/Al_2O_3$, mole ratio | 21.10 |

TABLE E

| Degrees 2-Theta | Interplanar d-Spacing (A) | $I/I_o$ |
| --- | --- | --- |
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |

TABLE E-continued

| Degrees 2-Theta | Interplanar d-Spacing (A) | $I/I_o$ |
| --- | --- | --- |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| | Example | | |
| --- | --- | --- | --- |
| | 3 | 4 | 5 |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2O/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| N-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution was added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table G:

TABLE G

| Product Composition (uncalcined) | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| n-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material ion-exchanged 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

$SiO_2B_2O_3 = 6.1$
$OH^-/SiO_2 = 0.06$
$H_2O/SiO_2 = 19.0$
$K/SiO_2 = 0.06$
$R/SiO_2 = 0.30$ where R is hexamethyleneimine.

The mixture was crystallized in a stainless steel reactor, with agitation, at 150° C. for 8 days. The crystalline product was filtered, washed with water and dried at 120°. C. A portion of the product was calcined for 6 hours at 240° C. and found to have the following sorption capacities:

$H_2O$ : 11.7 wt.%
Cyclohexane : 7.5 wt.%
n-Hexane : 11.4 wt.%

The surface area of the calcined crystalline material was measured (BET) to be 405 $m^2/g$.

The chemical composition of the uncalcined material was determined to be as follows:

N : 1.94 wt.%
Na : 175 ppm
K : 0.60 wt.%
Boron : 1.04 wt.%
$Al_2O_3$ : 920 ppm
$SiO_2$ : 75.9 wt.%
Ash : 74.11 wt.%
$SiO_2/Al_2O_3$, molar ratio : 1406
$SiO_2/(Al+B)_2O_3$, molar ratio : 25.8

EXAMPLE 12

A portion of the calcined crystalline product of Example 11 was treated with $NH_4Cl$ and again calcined. The final crystalline product was tested in the Alpha test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

$SiO_2/B_2O_3 = 12.3$
$OH^-/SiO_2 = 0.056$
$H_2O/SiO_2 = 18.6$
$K/SiO_2 = 0.056$
$R/SiO_2 = 0.30$ where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

$H_2O$ : 14.4 wt.%
Cyclohexane : 4.6 wt.%
n-Hexane : 14.0 wt.%

The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al + B)_2O_3$, molar ratio | 28.2 |

EXAMPLE 14

A portion of the calcined crystalline product of Example 13 was tested in the Alpha Test and found to have an Alpha Value of 5.

EXAMPLE 15

A ZSM-5 catalyst, in the hydrogen form having an Alpha Value of 350, was pelleted and sized to 24/40 mesh and then charged to the tubular reactor. The catalyst was pretreated by heating in air to 450° C. for 3 hours. The reactor was cooled to 200° C., and then flushed with nitrogen for 3 hours. Methanol and 2-methylnaphthalene were then admitted simultaneously and the temperature was raised to 270° C. and a balance was begun. After six hours, the balance was completed and the temperature was raised to 300° C. After a two-hour line-out period, another six hour balance was begun. This procedure was carried out successively at temperatures of 327°, 397°, 447°, 470° and 500° C.

Table H summarizes the results of the various balances. The data are reported on an oxygenate and water-free basis and do not account for the presence of unconverted methanol. There were no hydrocarbons with molecular weights less than naphthalene present in the products.

In this table conversion is calculated from a determination of hydrocarbons other than 2-methylnaphthalene. Selectivities are defined as the relative amount of specific hydrocarbons produced divided by the amount of non-methylnaphthalenes produced. This treatment eliminates the effect of methylnaphthalene isomerization on the conversion and selectivity determinations.

EXAMPLE 16

An MCM-22 catalyst prepared as in Example 7 and made into the hydrogen form having an Alpha Value of 360 was pelleted and sized to 24/40 mesh in the same manner as the catalyst in Example 15. The catalyst was pretreated by heating in air to 450° C. for 3 hours. The reactor was cooled to 200° C., and then flushed with nitrogen for 3 hours. Methanol and 2-methylnaphthalene were then admitted simultaneously and the temperature was raised to 271° C. and a balance was begun. After six hours, the balance was completed and the temperature was raised to 287° C. After a two-hour line-out period, another six hour balance was begun. This procedure was carried out successively at temperatures of 315°, 325°, 349°, 375° and 395° C.

The results of the product analyses from these successive balances are summarized in Table I.

Figure 2:
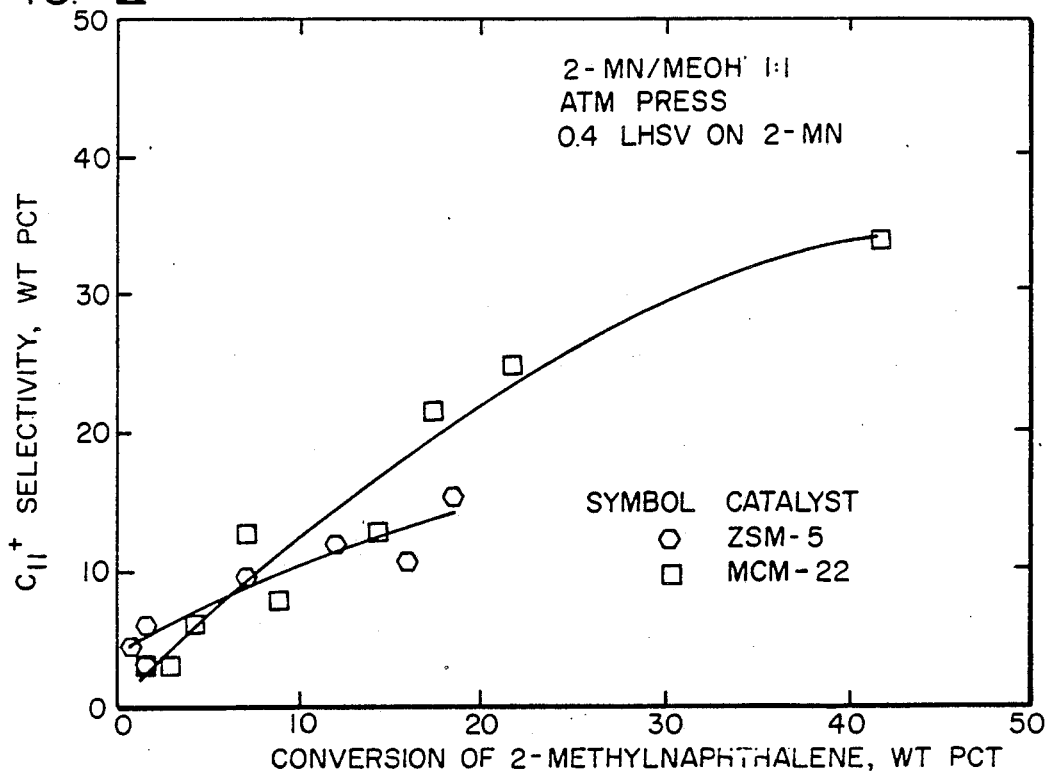
FIG. 2 graphically illustrates $C_{11}{}^+$ selectivity for the MCM-22 catalyzed embodiment of the present process and a ZSM-5 catalyzed process over a range of conversions.

FIGS. 1 and 2 compare the selectivities of the ZSM-5 and MCM-22 catalysts for 2,6-dimethylnaphthalene and $C_{11}+$ hydrocarbons, respectively. FIG. 1 shows that while the ZSM-5 catalyst is more selective for 2,6-dimethylnaphthalene at low conversions, the MCM-22 catalyst has a significantly higher selectivity for this isomer at 2-methylnaphthalene conversions greater than 20%. Operation at low conversions (<10%) would entail substantial downstream separation and recycle of unconverted 2-methylnaphthalene. For this reason the MCM-22 catalyst would be preferred where large quantities of this isomer are desired. The overall space-time yield of 2,6-dimethylnaphthalene is higher with the MCM-22 catalyst than with the ZSM-5 catalyst. An equilibrium mixture of dimethylnaphthalenes contains approximately 9 wt% of the 2,6-dimethylnaphthalene isomer.

FIG. 2 shows that the selectivity for undesirable tri-and tetra-alkylated naphthalenes is similar for both catalysts.

EXAMPLE 17

Figure 3:
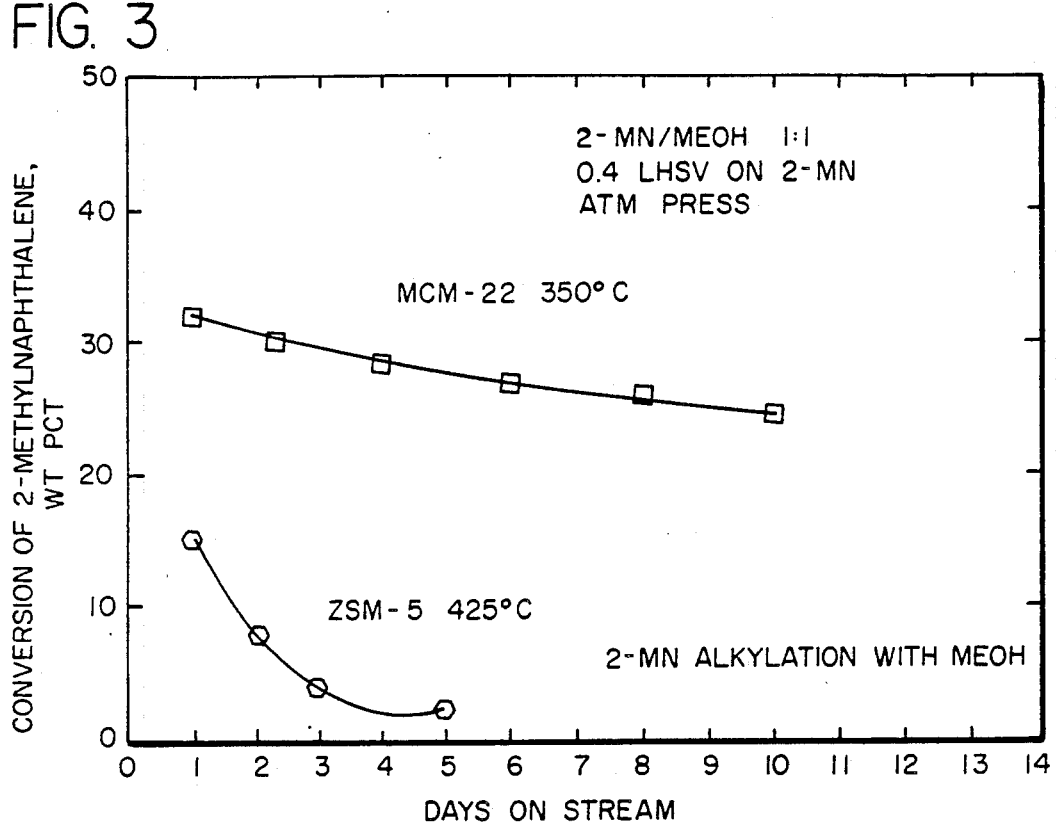
FIG. 3 is a graphical comparison of aging rates for the MCM-22 catalyzed embodiment of the present process and a ZSM-5 catalyzed process over a range of conversions.

A fresh sample of the same ZSM-5 catalyst used in Example 15 was streamed with 2-methylnaphthalene and methanol under the same conditions as described above except that the temperature was maintained constant at 425° C. from the beginning of the run. The conversion of 2-methylnaphthalene was determined by analyzing samples taken at the beginning of each day over the course of five days. FIG. 3 shows the conversion data vs. time on stream.

EXAMPLE 18

A fresh sample of the same MCM-22 catalyst used in Example 16 was streamed with 2-methylnaphthalene and methanol under the same conditions as described above except that the temperature was maintained constant at 350° C. from the beginning of the run. The conversion of 2-methylnaphthalene was determined by analyzing samples taken at the beginning of each day over the course of five days. FIG. 3 shows conversion data vs time on stream and compares this with the performance of the ZSM-5 catalyst. These data show that at approximately equivalent Alpha Values, the MCM-22 is the more stable and more active catalyst. At the higher temperatures required to obtain any appreciable conversion the ZSM-5 catalyst ages substantially.

TABLE H

Methylnaphthalene Alkylation with MeOH over ZSM-5
(atm pressure, 4 g/hr 2-MN, 4 g/hr MeOH, 10 cc of catalyst)

| Retention Time (seconds) | Component | 122-5-1 270° C. ZSM-5 | 122-5-5 300° C. ZSM-5 | 122-5-6 327° C. ZSM-5 | 122-5-7 397° C. ZSM-5 | 122-5-8 447° C. ZSM-5 | 122-5-9 470° C. ZSM-5 | 122-5-10 500° C. ZSM-5 |
|---|---|---|---|---|---|---|---|---|
| 1823 | Naphthalene | 0.01 | 0.01 | 0.03 | 0.04 | 0.04 | 0.05 | 0.08 |
| 2051.6 | 2-Me Naphtht. | 95.64 | 95.14 | 94.88 | 89.70 | 85.31 | 80.87 | 76.26 |
| 2080.1 | 1-Me Naphth. | 3.24 | 3.40 | 3.45 | 3.43 | 3.45 | 4.30 | 4.41 |
| 2092.1 | Ethyl Naphth. | 0.06 | 0.05 | 0.03 | 0.03 | 0.04 | 0.04 | 0.04 |
| 2240.7 | 2,6 DMN2,6 DMN | 0.47 | 0.59 | 0.72 | 2.07 | 2.83 | 2.97 | 3.28 |
| 2245.2 | 2,7 DMN2,7 DMN | 0.14 | 0.22 | 0.27 | 1.08 | 1.76 | 2.15 | 2.53 |
| 2269.5 | 1,7 + 1,3 DMN | 0.04 | 0.03 | 0.12 | 0.84 | 1.17 | 1.37 | 1.84 |
| 2275.6 | 1,6 DMN | 0.02 | 0.02 | 0.07 | 0.46 | 0.94 | 1.67 | 2.02 |
| 2302.5 | 2,3 + 1,4 DMN | 0.05 | 0.10 | 0.10 | 0.51 | 0.93 | 1.40 | 1.57 |
| 2312.6 | 1,5 DMN | <0.01 | <0.01 | <0.01 | 0.01 | 0.02 | 0.04 | 0.06 |
| 2319.7 | 1,8 DMN | <0.01 | <0.01 | <0.01 | <0.01 | <0.01 | <0.01 | <0.01 |
| 2328.3 | 1,2 DMN | 0.05 | 0.07 | 0.17 | 0.91 | 1.94 | 2.60 | 3.03 |
| 2440+ | Trimethyls | 0.07 | 0.08 | 0.09 | 0.64 | 1.27 | 1.86 | 2.72 |
|  | other Aromatics | 0.21 | 0.29 | 0.07 | 0.28 | 0.30 | 0.68 | 2.16 |

TABLE H-continued

Methylnaphthalene Alkylation with MeOH over ZSM-5
(atm pressure, 4 g/hr 2-MN, 4 g/hr MeOH, 10 cc of catalyst)

| Retention Time (seconds) | Component | 122-5-1 270° C. ZSM-5 | 122-5-5 300° C. ZSM-5 | 122-5-6 327° C. ZSM-5 | 122-5-7 397° C. ZSM-5 | 122-5-8 447° C. ZSM-5 | 122-5-9 470° C. ZSM-5 | 122-5-10 500° C. ZSM-5 |
|---|---|---|---|---|---|---|---|---|
| | (monocyclics) | | | | | | | |
| | Total Dimethyls | 0.77 | 1.03 | 1.45 | 5.88 | 9.95 | 12.20 | 14.33 |
| | 2,6 Dimethyl/Total Dimethyl, % | 61.0 | 57.3 | 49.7 | 35.2 | 29.5 | 24.3 | 22.9 |
| | MN Conversion, wt % | 1.1 | 1.5 | 1.7 | 6.9 | 11.3 | 14.8 | 19.3 |
| | DMN Selectivity, % | 69.3 | 83.2 | 86.8 | 85.4 | 85.1 | 82.1 | 80.0 |
| | 2,6-DMN Selectivity, % | 42.0 | 40.4 | 43.1 | 30.0 | 25.0 | 20.1 | 17.0 |
| | 2,6 + 2,7 DMN Selectivity, % | 55.5 | 55.5 | 58.2 | 45.7 | 40.6 | 34.6 | 30.1 |
| | $C_{11}$ + Selectivity, % | 6.4 | 5.3 | 5.3 | 9.3 | 11.2 | 12.6 | 14.1 |
| | MN Isomeriztion* | 0.04 | 0.21 | 0.26 | 0.24 | 0.26 | 1.13 | 1.25 |
| | (1MN/2MN) × 100 | 3.34 | 3.6 | 3.6 | 3.8 | 4.0 | 5.3 | 5.8 |

*Note: 2-Methylnaphthalene feed contained 3.20 wt % 1-Methylnaphthalene as impurity.

TABLE I

Methylnaphthalene Alkylation with MeOH over MCM-22
(Atm pressure, 4 g/hr 2-MN, 4 g/hr MeOH, 10 cc of catalyst)

| Retention Time (seconds) | Component | 122-4-1 271° C. MCM-22 | 122-4-2 271° C. MCM-22 | 122-4-3 287° C. MCM-22 | 122-4-5 315° C. MCM-22 | 122-4-8 349° C. MCM-22 | 122-4-9 375° C. MCM-22 | 122-5-10 395° C. MCM-22 | 122-4-5 325° C. MCM-22 |
|---|---|---|---|---|---|---|---|---|---|
| 1823 | Naphthalene | 0.03 | 0.03 | 0.03 | 0.03 | 0.03 | 0.05 | 0.29 | 0.04 |
| 2051.6 | 2-Me Naphth. | 93.72 | 94.83 | 91.26 | 87.28 | 83.16 | 61.57 | 43.21 | 79.23 |
| 2080.1 | 1-Me Naphth. | 3.66 | 3.53 | 3.99 | 4.80 | 6.40 | 9.01 | 13.65 | 6.17 |
| 2092.1 | Ethyl Naphth. | 0.07 | 0.07 | 0.03 | 0.02 | 0.05 | 0.04 | 0.03 | 0.03 |
| 2240.7 | 2,6 DMN | 0.16 | 0.16 | 0.58 | 0.90 | 3.30 | 6.23 | 10.18 | 2.34 |
| 2245.2 | 2,7 DMN | 0.08 | 0.12 | 0.45 | 0.73 | 2.52 | 3.24 | 4.47 | 1.00 |
| 2269.5 | 1,7 + 1,3 DMN | 0.34 | 0.25 | 0.66 | 1.20 | 3.29 | 4.23 | 6.17 | 2.62 |
| 2275.6 | 1,6 DMN1,6 DMN | 0.26 | 0.18 | 0.33 | 0.35 | 0.38 | 0.46 | 0.53 | 0.37 |
| 2302.5 | 2,3 + 1,4 DMN | 0.43 | 0.34 | 0.56 | 1.10 | 3.04 | 3.24 | 4.47 | 1.97 |
| 2312.6 | 1,5 DMN | 0.18 | 0.16 | 0.33 | 0.55 | 1.13 | 1.24 | 1.82 | 1.07 |
| 2319.7 | 1,8 DMN | <0.01 | <0.01 | 0.02 | 0.03 | 0.03 | 0.05 | 0.06 | 0.04 |
| 2328.3 | 1,2 DMN | 0.68 | 0.48 | 1.09 | 1.99 | 2.97 | 5.16 | 6.20 | 3.14 |
| 2440+ | Trimethyls | 0.08 | 0.05 | 0.37 | 0.85 | 2.10 | 5.38 | 8.52 | 12.55 |
| | other Aromatics (monocyclics) | 0.31 | 0.30 | 0.30 | 0.60 | — | — | — | — |
| | Total Dimethyls | 2.13 | 1.69 | 4.02 | 6.90 | 17.66 | 23.85 | 33.9 | 12.55 |
| | 2,6 Dimethyl/Total Dimethyl, % | 7.5 | 9.5 | 14.4 | 13.1 | 18.7 | 26.1 | 30.0 | 18.6 |
| | MN Conversion, wt % | 2.6 | 2.1 | 4.8 | 7.9 | 20.4 | 29.4 | 43.1 | 14.6 |
| | DMN Selectivity, % | 81.3 | 79.0 | 84.6 | 87.1 | 86.4 | 81.1 | 78.6 | 85.9 |
| | 2,6-DMN Selectivity, % | 6.1 | 7.5 | 12.2 | 13.0 | 16.1 | 21.2 | 23.6 | 16.9 |
| | 2,6 + 2,7 DMN Selectivity, % | 9.2 | 13.1 | 21.7 | 20.6 | 28.5 | 32.2 | 34.0 | 22.9 |
| | $C_{11}$ + Selectivity, % | 3.1 | 2.3 | 7.8 | 12.3 | 10.3 | 18.3 | 19.8 | 11.4 |
| | MN Isomeriztion* | 0.5 | 0.3 | 0.8 | 1.7 | 3.3 | 6.0 | 10.8 | 3.1 |
| | (1MN/2MN) × 100 | 3.9 | 3.7 | 4.4 | 5.4 | 8.7 | 14.6 | 31.6 | 7.8 |

*Note: 2-Methylnaphthalene feed contained 3.20 wt % 1-Methylnaphthalene as impurity.

The above examples illustrate that in a process for preparing dialkylnaphthalenes from a feedstock of 2-methylnaphthalene with alkylating agent, e.g. methanol, using zeolite MCM-22 as the alkylation catalyst produces unexpectedly different results from using ZSM-5. MCM-22 is more selective than ZSM-5 for the production of the 2,6-DMN isomer at higher conversions, and MCM-22 has significantly better aging properties.

What is claimed is:

1. A process for producing 2,6-dialkylnaphthalene from a feedstock comprising 2-alkylnaphthalene and an alkylating agent having at least one alkylating aliphatic group of from one to five carbon atoms said process comprising contacting said feedstock with a catalyst composition under alkylation conditions to produce an alkylate containing 2,6-dialkylnaphthalene, said catalyst composition comprising a synthetic zeolite characterized by an X-ray diffraction pattern including interplanar d-spacings as set forth in Table A of the specification.

2. The process of claim 1 wherein said zeolite is characterized by an X-ray diffraction pattern including interplanar d-spacings as set forth in Table B of the specification.

3. The process of claim 1 wherein the zeolite is characterized by an X-ray diffraction pattern including interplanar d-spacings as set forth in Table C of the specification.

4. The process of claim 1 wherein the zeolite is characterized by an X-ray diffraction pattern including interplanar d-spacings as set forth in Table D of the specification.

5. The process of claim 1 wherein the synthetic zeolite has a composition comprising the molar relationship:

$$X_2O_3(n)YO_2$$

wherein X is a trivalent element selected from the group consisting of aluminum, boron, iron and gallium, Y is a tetravalent element selected from the group consisting of silicon and germanium, and n is at least about 10.

6. The process of claim 1 wherein said synthetic zeolite has been treated to replace original ions, at least in part, with an ion or mixture of ions selected from the group consisting of hydrogen, rare earth metals, and metals of Groups IIA, IIIA, IVA, IB, IIB, IIIB, IVB, VIB and VIII of the Periodic Table.

7. The process of claim 1 wherein said synthetic zeolite has been thermally treated at a temperature of up to about 925° C.

8. The process of claim 1 wherein the 2-alkylnaphthalene is 2-methylnaphthalene.

9. The process of claim 1 wherein the alkylating agent is selected from the group consisting of monoalcohols, dialcohols, trialcohols, olefins, aldehydes, halides, and ethers.

10. The process of claim 1 wherein the alkylating agent is methanol.

11. The process of claim 1 wherein the 2,6-dialkylnaphthalene is 2,6-dimethylnaphthalene.

12. The process of claim 1 wherein said feedstock additionally comprises naphthalene.

13. The process of claim 1 wherein said alkylation conditions include a temperature of from about 0° C. to about 500° C., a pressure of from about 0 to about 250 atmospheres and a liquid hourly space velocity of from about 0.1 $hr^{-1}$ to about 10 $hr^{-1}$.

14. The process of claim 1 wherein said alkylation conditions include a temperature of from about 240° C. to about 450° C., a pressure of from about 1 atmosphere to about 25 atmospheres and a liquid hourly space velocity of from about 0.1 $hr^{-1}$ to about 1 $hr^{-1}$.

15. The process of claim 1 wherein the molar ratio of alkylating agent to 2-alkylnaphthalene is from about 1:1 to about 10:1.

16. The process of claim 1 wherein the molar ratio of alkylating agent to 2-alkylnaphthalene is from about 3:1 to about 5:1.

17. The process of claim 1 wherein said contacting of the feedstock with the catalyst under alkylation conditions is carried out in a tubular downflow reaction with a fixed bed of catalyst.

18. A process for preparing 2,6-dimethylnaphthalene from 2-methylnaphthalene comprising contacting said 2-methylnaphthalene with methanol under alkylation conditions including a temperature of from about 0° C. to about 500° C., a pressure of from about 0 to about 250 atmospheres, a liquid hourly space velocity of from about 0.1 $hr^{-1}$ to about 10 $hr^{-1}$ and a methanol to 2-methylnaphthalene mole ratio of from about 1:1 to about 10:1, with a catalyst composition comprising a synthetic zeolite characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

19. The process of claim 1 wherein said catalyst composition comprises a matrix material.

20. The process of claim 19 wherein said matrix material is selected from the group consisting of silica-containing material, alumina-containing material, zirconia-containing material, titania-containing material, magnesia-containing material, beryllia-containing material, thoria-containing material, and combinations thereof.

* * * * *

UNITED STATES PATENT AND TRADEMARK OFFICE
CERTIFICATE OF CORRECTION

PATENT NO. :     5,001,295

DATED      :     March 19, 1991

INVENTOR(S) :    P.J. Angevine et al.

It is certified that error appears in the above-identified patent and that said Letters Patent is hereby corrected as shown below:

Col. 5, line 57, "2" should be --20--

Col. 15-16, Table H, line 16, "Isomeriztion" should be --Isomerization--

Col. 15-16, Table H, line 9, "9.95" should be --9.59--

Col. 15-16, Table I, line 48, "Isomeriztion" should be --Isomerization--

Signed and Sealed this

Eighth Day of September, 1992

Attest:

DOUGLAS B. COMER

Attesting Officer

Acting Commissioner of Patents and Trademarks